United States Patent
Chattaraj et al.

(10) Patent No.: US 10,194,864 B2
(45) Date of Patent: Feb. 5, 2019

(54) ANCHORING APPARATUS AND METHOD FOR ATTACHING DEVICE ON BODY

(71) Applicant: Medtronic MiniMed, Inc., Northridge, CA (US)

(72) Inventors: Sarnath Chattaraj, Simi Valley, CA (US); Kiem Dang, Thousand Oaks, CA (US); Poonam S. Gulati, La Canada, CA (US); James Shallenberger, Granada Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 806 days.

(21) Appl. No.: 13/924,038

(22) Filed: Jun. 21, 2013

(65) Prior Publication Data

US 2014/0378799 A1     Dec. 25, 2014

(51) Int. Cl.

| | |
|---|---|
| *A61B 5/00* | (2006.01) |
| *B32B 3/06* | (2006.01) |
| *A61B 5/15* | (2006.01) |
| *A61B 5/155* | (2006.01) |
| *A61B 5/157* | (2006.01) |
| *A61M 5/142* | (2006.01) |
| *B32B 5/02* | (2006.01) |
| *B32B 5/06* | (2006.01) |
| *B32B 5/26* | (2006.01) |
| *B32B 7/12* | (2006.01) |

(Continued)

(52) U.S. Cl.
CPC ............ *A61B 5/6833* (2013.01); *A61B 5/155* (2013.01); *A61B 5/157* (2013.01); *A61B 5/150022* (2013.01); *A61B 5/150389* (2013.01); *A61B 5/150503* (2013.01); *A61B 5/150755* (2013.01); *A61B 5/150992* (2013.01); *A61M 5/14248* (2013.01); *B32B 3/02* (2013.01); *B32B 3/06* (2013.01); *B32B 5/022* (2013.01); *B32B 5/06* (2013.01); *B32B 5/26* (2013.01); *B32B 7/12* (2013.01); *A61B 5/14532* (2013.01); *B32B 2255/10* (2013.01); *B32B 2535/00* (2013.01); *Y10T 428/24008* (2015.01); *Y10T 428/24017* (2015.01)

(58) Field of Classification Search
None
See application file for complete search history.

(56) References Cited

U.S. PATENT DOCUMENTS

| | | | |
|---|---|---|---|
| 4,333,468 A * | 6/1982 | Geist | A61M 25/02 128/DIG. 26 |
| 4,755,173 A | 7/1988 | Konopka et al. | |

(Continued)

*Primary Examiner* — Jacqueline Cheng
*Assistant Examiner* — Jairo Portillo
(74) *Attorney, Agent, or Firm* — Medtronic MiniMed, Inc.

(57) ABSTRACT

The present invention describes improved systems and methods for attaching external medical devices to the body of a patient using a multilayer attachment apparatus. Medical devices that require attachment to the body, including monitoring devices, drug-infusing devices and the like, can utilize embodiments of the attachment apparatus and method described herein. Embodiments of the invention include new adhesive and hook and loop attachment mechanisms and methods for using embodiments of the multilayer attachment apparatus to attach medical device and/or medical device components to the body.

26 Claims, 6 Drawing Sheets

(51) Int. Cl.
  *B32B 3/02* (2006.01)
  *A61B 5/145* (2006.01)

(56) References Cited

U.S. PATENT DOCUMENTS

| | | | |
|---|---|---|---|
| 5,163,442 A * | 11/1992 | Ono | A61B 5/150022 |
| | | | 600/565 |
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,585,707 B2 | 7/2003 | Cabiri et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,789,836 B2 * | 9/2010 | Van Wyk | A61B 5/02411 |
| | | | 600/304 |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 2007/0049865 A1 * | 3/2007 | Radmer | A61M 5/14248 |
| | | | 604/93.01 |
| 2007/0123819 A1 | 5/2007 | Mernoe et al. | |
| 2007/0232864 A1 * | 10/2007 | Sharp | A61B 17/02 |
| | | | 600/227 |
| 2009/0088614 A1 * | 4/2009 | Taub | A61B 5/14532 |
| | | | 600/316 |
| 2009/0326417 A1 * | 12/2009 | Ales, III | A61F 13/84 |
| | | | 600/584 |
| 2010/0160861 A1 | 6/2010 | Causey, III et al. | |
| 2010/0331646 A1 * | 12/2010 | Hoss | A61B 5/14503 |
| | | | 600/347 |
| 2011/0112458 A1 * | 5/2011 | Holm | A61L 15/58 |
| | | | 602/54 |

\* cited by examiner

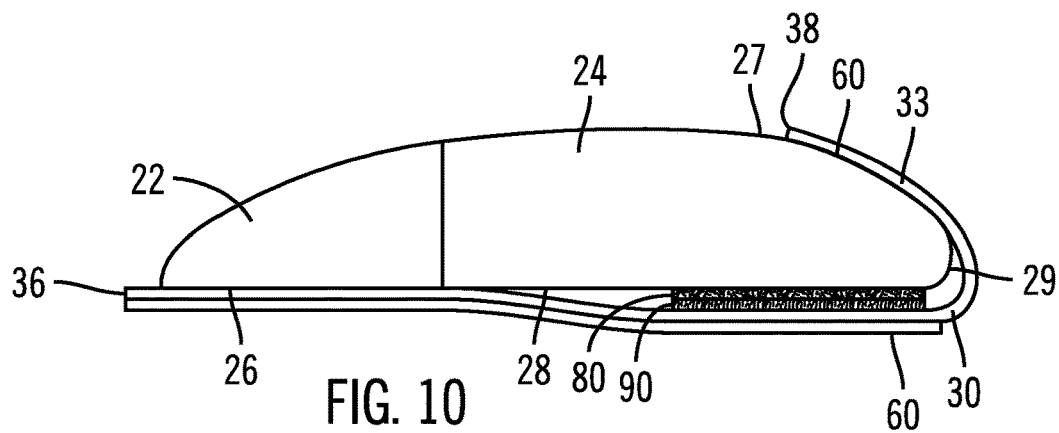
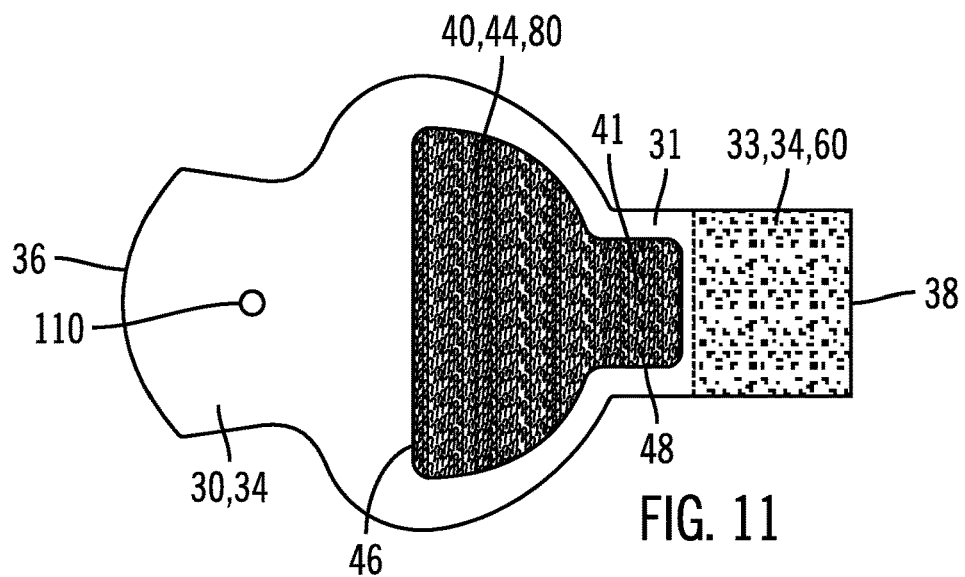
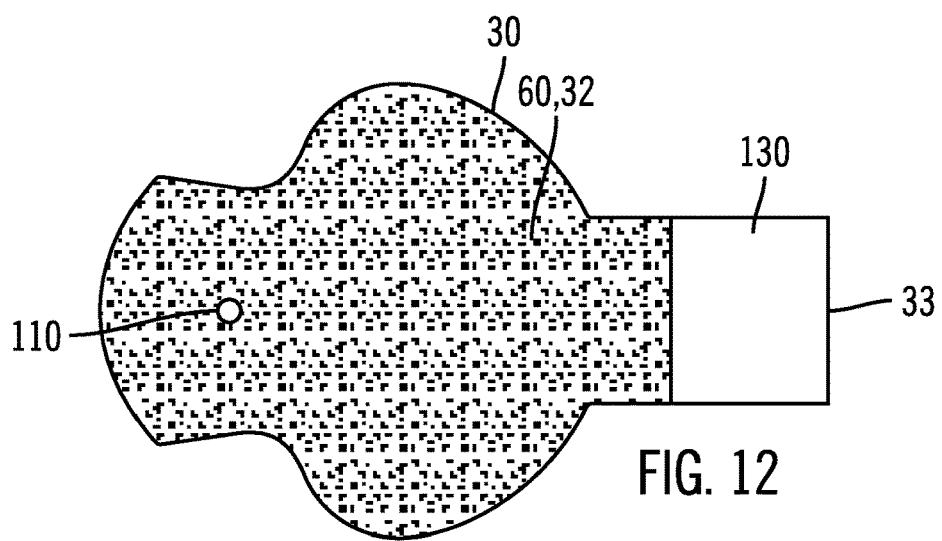

ANCHORING APPARATUS AND METHOD FOR ATTACHING DEVICE ON BODY

FIELD OF THE INVENTION

This invention relates to a new apparatus and method for attaching a medical device on a body, and in particular embodiments, to an apparatus and method for anchoring a medical device on a body utilizing improved adhesive and hook and loop attachments.

BACKGROUND OF THE INVENTION

Certain chronic diseases can be monitored and treated in a continuous manner or at particular times throughout the day using medical devices that externally attach to the body. Medical devices that are connected to the body externally require a robust and stable connection that can last for one or more days of wear while providing consistent and accurate monitoring or treatment.

For example, a patient can utilize external sensor devices that connect a sensor to the body to monitor his or her condition. The connection of external sensor devices to the body must be stable to obtain accurate physiological readings of the patient. Delivery devices can also be externally connected to the body to deliver medication. The connection of external delivery devices to the body must be steady enough to allow consistent fluid-flow communication of the medication from the device to the body. If the attachment of the delivery device to the body is disrupted, loss of medication can occur or inaccurate dosages of medication can be delivered to the body.

As a non-limiting example, diabetic patients monitor their blood glucose (BG) levels and deliver insulin continuously or at certain times throughout the day utilizing external devices. The diabetic patient measures his or her BG level using a BG measurement device to determine if treatment is needed, be it with glucose to raise glucose levels or insulin to lower glucose levels. The diabetic patient may use a continuous glucose measurement or monitoring system to monitor sensor glucose (SG) throughout the day. To deliver the insulin to the body, the diabetic patients use insulin delivery devices, including external infusion pumps or patches. Both monitoring and delivery devices should be connected to the body in a stable manner to obtain accurate sensor readings and provide correct delivery dosages.

Current methods of attaching medical devices to the skin or body of the patient utilize adhesive. The adhesive is applied on the device and adheres to the body. Adhesive methods of attachment alone can lose effectiveness in adhering to the body for patients living in geographical areas of high humidity or for patients living active lifestyles. Because of the instability of the attachment of the external device to the body, the operation of devices, which are sensitive to movement, can be compromised. The devices can detach and fall off the body due to lack of adhesion and the patients are thus not able to utilize the important diagnostic and therapeutic tools. Again, the devices can provide inaccurate sensor readings and send erroneous data to a delivery device, or could result in loss of medication at the delivery site into the body.

The current methods of attachment of external devices also do not address the problems associated with anchoring a rigid inflexible device to the curved contours of the body. In addition, devices that merely increase adhesion strength to overcome instability issues can be difficult to remove from the body. It is desirable to provide an attachment apparatus, system and method to improve performance and increase the accuracy of sensor and delivery devices that are connected to the body.

BRIEF SUMMARY OF THE INVENTION

Embodiments of the present invention provide apparatuses, systems and methods for attaching external medical devices to the body of a patient, which obviate for practical purposes, the above mentioned limitations. According to an embodiment of the invention, the apparatus for anchoring a medical device to a body of a user comprises a nonwoven layer having a bottom surface and a top surface, a first fastener material layer and a second fastener material layer. Each of the first and second fastener material layers also have a bottom surface and a top surface. At least a portion of the bottom surface of the first fastener material layer can be connected to at least a portion of the top surface of the nonwoven layer in a removable manner. The top surface can connect to at least a portion of the medical device.

In some embodiments, at least a portion of the bottom surface of the nonwoven layer includes an adhesive material adapted to attach to the body of the user. In other embodiments, the apparatus includes an adhesive layer having a bottom surface and a top surface, where the bottom surface of the adhesive layer can be adapted to attach to the body of the user and at least a portion of the bottom surface of the nonwoven layer can be connected to the top surface of the adhesive layer.

Further embodiments include a first fastener material layer having a plurality of loop elements and the second fastener material layer having a plurality of hook elements. Yet further embodiments include a first fastener material layer having a plurality of hook elements and the second fastener material layer having a plurality of loop elements.

In specific embodiments, at least a portion of the top surface of the nonwoven layer is connectable to at least a portion of the medical device. In embodiments where the medical device includes a cannula, the nonwoven layer can include an aperture adapted to receive the cannula. In further embodiments, the nonwoven layer includes a poly layer on at least a portion of its top surface. The poly layer can cover the entire surface area or only a portion of the top surface of the nonwoven layer. In specific embodiments, the poly layer is a thin film coating of polyurethane.

In yet further embodiments, the apparatus can include at least one removable liner to cover at least a portion of the bottom surface of the nonwoven layer to protect the adhesive prior to use. The liner can include a tab to help remove the liner from the adhesive.

In additional embodiments, the nonwoven layer includes a first end and a second end. The top surface of the nonwoven layer at the first end is connectable to the medical device and the top surface of the nonwoven layer at the second end is connectable to at least a portion of the bottom surface of the first fastener material. In further embodiments, the nonwoven layer can include a tab to assist with application and removal of the apparatus, for example, when used with a disposable or reusable device. In still further embodiments, the nonwoven layer can include an extended tab. In some embodiments, a top surface of the nonwoven layer at the extended tab includes a fastening material to attach the extended tab to a surface of the medical device. In embodiments, the bottom surface of the nonwoven layer at the extended tab can include a poly layer.

In yet further embodiments, the first fastener material layer can include a first end and a second end. The first end of the bottom surface of the first fastener material layer can be connected to at least a portion of the top surface of the nonwoven layer. In additional embodiments, the first fastener material layer can include a tab. In other embodiments, the bottom surface of the first fastener material can include an adhesive material. In still other embodiments, the second fastener material layer can include a tab. In further embodiments, the top surface of the second fastener material layer can include an adhesive material.

In certain embodiments, the medical device to which the attachment apparatus connects can include a first component and a second component. The first and second components can be removably attachable with one another in embodiments. At least a portion of the top surface of the nonwoven layer can connect to the first component of the medical device and at least a portion of the top surface of the second fastener material layer can connect to the second component of the medical device. In specific embodiments, the medical device can be a glucose monitoring device, the first component can be a sensor base, and the second component can be a sensor transmitter.

In another embodiment, a system for improved glucose sensor monitoring device performance and accuracy is described. In some embodiments the system includes a glucose monitoring device including a sensor transmitter and a sensor base having a cannula and glucose sensor. An attachment apparatus is included in the system to attach the glucose monitoring device to a body of a user. In embodiments, the attachment apparatus can include a nonwoven layer having a first end, a second end, a bottom surface and a top surface, where the bottom surface of the nonwoven layer can include adhesive to attach the nonwoven layer to the body. The top surface at the first end of the nonwoven layer can be connected to the sensor base and the first end of the nonwoven layer can further include an aperture to receive the cannula of the sensor. The apparatus can also include a first fastener material layer and a second fastener material layer that are removably connected to one another. For example, at least a portion of the top surface of the first fastener layer can be connected to a bottom surface of the second fastener layer. At least a portion of a bottom surface of the first fastener material layer can be connected to at least a portion of a top surface of the second end of the nonwoven layer. The top surface of the second fastener material layer can be connected to the sensor transmitter, thereby attaching the glucose monitoring device to the body when the first and second fastener layers are connected and at least a portion of the nonwoven layer of the attachment apparatus is attached to the body.

Embodiments of methods for anchoring an attachment apparatus to the body are also described herein by way of the embodiments described above. Other features and advantages of the invention will become apparent from the following detailed description, taken in conjunction with the accompanying drawings which illustrate, by way of example, various features of embodiments of the invention.

BRIEF DESCRIPTION OF SEVERAL VIEWS OF THE DRAWINGS

A detailed description of embodiments of the invention will be made with reference to the accompanying drawings, wherein like numerals designate corresponding parts in the several figures. The drawings are provided for illustrative purposes only and are not necessarily drawn to scale.

FIG. 10 is a side view of another representation of a multilayer attachment apparatus connected to a medical device in accordance with an embodiment of the present invention;

FIG. 11 is a top view of a further representation of a removable liner, nonwoven layer, and first fastener material layer of a multilayer attachment apparatus in accordance with an embodiment of the present invention;

FIG. 12 is a bottom view of a representation of a nonwoven layer of a multilayer attachment apparatus in accordance with an embodiment of the present invention;

DETAILED DESCRIPTION OF THE INVENTION

Figure 1:
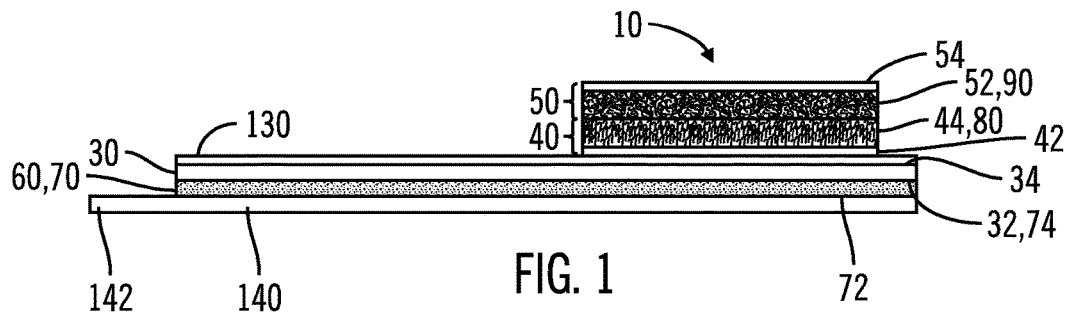
FIG. 1 is a side view of a representation of a multilayer attachment apparatus in accordance with an embodiment of the present invention.

As shown in the drawings for purposes of illustration, the invention is embodied in a new and improved apparatus, system and method for attaching a medical device to the body. The medical device can be configured to provide monitoring or treatment operation on a user while attached to the body. Medical devices that can utilize various embodiments of the improved attachment apparatus and method relate generally to medical devices such as, but not limited to sensors, physiological characteristic monitors and infusion medium delivery systems, devices and methods that can include cannula or needle inserting devices and methods.

Devices according to embodiments of the present invention can be used with, connectable to and disconnectable from or incorporated in a portion of a medical device system. As a non-limiting example, a needle inserting device can be connected to a base structure of an infusion delivery device for insertion of a needle, after which the needle inserting device can be removed from the base and replaced with a different device component such as, but not limited to a reservoir and pump or drive device can be coupled to the base for operation. For example, a sensor or delivery medical device and method may operate to insert a cannula or needle through a user's skin to convey a fluid from the user to one or more sensor elements and/or to provide a fluid flow path for conveying an infusion medium through a hollow channel in the cannula or needle and into the user. Embodiments can also be configured to provide a contiguous fluid-flow passage for fluid transfer between a reservoir and the user when the hollow needle or cannula is inserted in the user. For example, the user could use the multilayer attachment apparatus and method with infusion delivery devices and systems. As a non-limiting example, the apparatus can be used with any insulin infusion pump, patch, insulin infusion set and the like that is used externally on the body of a user. The apparatus could also be used with patch devices generally described by way of example in U.S. Pat. No. 8,323,250 filed Feb. 7, 2008, entitled "Adhesive patch systems and methods," the disclosure of which is herein incorporated by reference in its entirety.

In some embodiments, the medical device can include one or more components. In embodiments, at least a portion of a medical device can be adapted to be secured to the user during operation of the medical monitoring or treatment device and another portion of the medical device may be removable during operation of the device. Certain embodiments may be directed to use of the attachment apparatus and method with a sensor monitoring system. Such embodiments can be used with a sensor having a sensor base with a cannula that can be inserted into the skin of a user and a sensor transmitter that is connectable to and disconnectable from the sensor base while the base remains attached to the skin. The sensor can provide a signal indicative of a characteristic of a user and may be implanted in and/or through subcutaneous, dermal, sub-dermal, inter-peritoneal or peritoneal tissue. Embodiments of a surface mounted sensor could utilize interstitial fluid harvested from underneath the skin. In specific embodiments of the present invention, the sensor can determine glucose levels in the blood and/or body fluids of the user. However, it will be recognized that further embodiments of the invention may be used to determine the levels of other agents, characteristics or compositions, such as hormones, cholesterol, medication concentrations, pH, oxygen saturation, viral loads (e.g., HIV), or the like. Embodiments may provide sensor readings on an intermittent or continuous basis.

The sensor can be an electrode-type sensor, or other type of sensor, such as chemical based, optical based or the like. The sensor transmitter can store and provide sensor readings to other devices or other components of a sensor system. For example, the transmitter can process and wirelessly transmit sensor signals to a remotely located data receiving device. Some embodiments can allow a user or a physician to disconnect the sensor transmitter from the sensor base to retrieve sensor readings. In other embodiments, the sensor controller and/or sensor transmitter used with the multilayer attachment apparatus need not be disconnected from the sensor base during operation and can be connected for the entire duration of wear. In further embodiments, the sensor base and sensor transmitter can be manufactured as one medical device instead of multiple components.

As a non-limiting example, the user could use the multilayer attachment apparatus and method with a continuous glucose measurement or monitoring system, including, but not limited to Medtronic MiniMed, Inc. products such as Sof-Sensor®, Enlite®, iPro®, and MiniLink® transmitter. The apparatus could also be used with sensor and sensor transmitters generally described by way of example in U.S. Pat. No. 5,954,643, filed Jun. 9, 1997, entitled "Insertion Set for a Transcutaneous Sensor," U.S. Pat. No. 6,248,067, filed Feb. 5, 1999, entitled "Analyte Sensor and Holter-type Monitor System and Method of Using the Same," and U.S. Pat. No. 6,809,653, filed Dec. 17, 1999, entitled "Telemetered Characteristic Monitor System and Method of Using the Same," the disclosures of which are herein incorporated by reference in their entireties.

As generally shown in FIGS. 1-15, embodiments of the invention include a multi-layer attachment apparatus 10 including a plurality of nonwoven and fastener material layers. In all embodiments of the invention, adhesive bonding, backing adhesive, transfer adhesive, pressure sensitive adhesive, polyurethane medical tape, humidity-resistant adhesive, UV cure adhesive, ultrasonic welding, and/or other like attachment methods can be used to attach the plurality of layers of the attachment apparatus 10 to one another and/or to a medical device 20. Apparent from the accompanying figures, the drawings of the multilayer attachment apparatus 10 alone and drawings of the multilayer attachment device 10 connected to one or more components 22, 24 of a medical device 20 are not drawn to scale. Because the layers are thin in actual embodiments, the thickness of each layer is magnified in the drawings for illustrative purposes only. Thicknesses of the layers relative to the size of the medical devices and the medical device components are also not necessarily drawn to scale. For example, in embodiments, the attachment apparatus 10 can have hook and loop fastener material layers 40, 50 with adhesive backing and engaged with one another having a thickness ranging from approximately 0.0465 inches to 0.2500 inches, nominal at approximately 0.053 inches.

As shown in FIG. 1, an embodiment of the multi-layer attachment apparatus 10 for attachment of a medical device 20 to the body of a user includes a nonwoven layer 30 having a bottom surface 32 and a top surface 34. The nonwoven layer 30 can include any suitable nonwoven material and the like, including but not limited to any fabric-like material bonded together by entangling fiber or filaments (and by perforating films) chemically, thermally, or mechanically. In some embodiments, the nonwoven layer 30 can be replaced with a woven material layer or other suitable material. At least a portion of the bottom surface 32 of the nonwoven layer 30 can attach to the body of a user via an adhesive material 60 backing or an adhesive layer 70. For example, in some embodiments, the bottom surface 32 of the nonwoven layer 30 can include an adhesive material 60 for attaching the nonwoven layer 30 to the body of a user. In embodiments, the entire bottom surface 32 or a portion of the bottom surface 32 can include the adhesive material 60 backing. In other embodiments, the bottom surface 32 of the nonwoven layer 30 can be connected to an adhesive layer 70 to attach the apparatus 10 to the body of a user. The adhesive layer 70 can have a bottom surface 72 and a top surface 74, in which the bottom surface 72 can attach to the body and the top surface 74 can attach to the adhesive layer 70. The nonwoven layer 30 can be bonded or welded to the adhesive layer 70. The adhesive layer 70 as described herein need not be a separate layer from the nonwoven layer 30, but can include an adhesive backing on the nonwoven layer 30, for example, similar to that of a Band-Aid®.

Embodiments of the invention can include a first adhesive material to connect the plurality of layers of the attachment apparatus 10 to one another and/or to a medical device 20 and a second adhesive material to attach the attachment apparatus 10 to the body. In such embodiments, the first adhesive material should bind at least as strong as the second adhesive material that attaches to the skin of a user. In embodiments, testing of the adhesive material passed at least a seven day soak test in saline solution at 50° Celsius. The adhesive material 60 or adhesive layer 70 used to attach the nonwoven layer 30 to the body of the user can be any material suitable for use on the body 200. For example, a pressure sensitive adhesive, an acrylic, butyl, polyisobutylene, hydrogel, or silicone based adhesive, a medical grade adhesive, a double sided polyester film tape and the like can be used to attach the multilayer attachment apparatus 10 to the body 200.

In some embodiments, as illustrated in FIG. 1, the adhesive material 60 or adhesive layer 70 can include a removable liner 140 to protect the adhesive prior to attachment of the nonwoven layer 30 to the body. The removable liner 140 can include a tab 142 to allow for easier removal of the liner 140 from the adhesive material 60 or adhesive layer 70.

Also shown in FIG. 1, at least a portion of the top surface 34 of the nonwoven layer 30 can be connected to a first fastener material layer 40. The first fastener material layer 40 can have a bottom surface 42 and a top surface 44. In embodiments, the first fastener material layer 40 can comprise a nonwoven, woven or other suitable base material on its bottom surface 42 to which a fastener material such as hook or loop Velcro® elements 80, 90 can be attached and exposed on the top surface 44. The bottom surface 42 of the first fastener material layer 40 can be connected to at least a portion of the top surface 34 of the nonwoven layer 30. Adhesive bonding, backing adhesive, transfer adhesive, pressure sensitive adhesive, polyurethane medical tape, ultrasonic welding, and/or other like attachment methods can be used to attach the first fastener material layer 40 to the nonwoven layer 30. Some embodiments can include an adhesive material 60 on at least a portion of the top surface 34 of the nonwoven layer 30 or an adhesive material 60 or backing at least a portion of the bottom surface 42 of the first fastener material layer 40. In other embodiments, the nonwoven layer 30 can have a fastener material incorporated into the nonwoven material and form one layer having both the nonwoven material and fastener material.

In some embodiments and illustrated in FIG. 1, a poly layer 130 can be connected to at least a portion of the top surface 34 of the nonwoven layer 30, and between the nonwoven layer 30 and first fastener material layer 40, to provide a water-resistant coating and/or contain the adhesive backing of the first fastener material layer 40. The poly layer 130 can cover the entire surface area of the top surface 34 of the nonwoven layer 30 or can cover only a portion of the nonwoven layer 30. In specific embodiments, the poly layer 130 is a thin film coating of polyurethane. As defined herein, the poly layer can comprise polyurethane, polyolefin, polyester, polypropylene, polyethylene, polyacrylate polymer, and the like.

Also shown in embodiments in FIG. 1, a second fastener material layer 50 can be removably connected to the first fastener material layer 40. The second fastener material layer 50 can have a bottom surface 52 and a top surface 54. In embodiments, the second fastener material layer 50 can comprise a nonwoven material base or other suitable material on its top surface 54 to which a fastener material such as hook or loop Velcro® elements 80, 90 are attached and exposed on the bottom surface 52. In particular embodiments, the bottom surface 52 of the second fastener material layer 50 is removable attached to the top surface 44 of the first fastener material layer 40. The first and second fastener material layers 40, 50 provide a mechanism for detachment and reattachment of the fastener material layers from and to one another.

The fastener materials of the fastener material layers 40, 50 can include, but are not limited to hook and loop fastener materials such as Velcro® and other fastener materials including adhesive material, mushroom stem hook to hook fasteners (e.g., 3M™ Dual Lock™) magnetic material, clips, snaps, male/female attachment mechanisms and the like. For example, the first fastener material layer 40 can include a plurality of loop elements 80 on its top surface 44 and the second fastener material layer 50 can include a plurality of hook elements 90 on its bottom surface 52. Or vice versa, in other embodiments, the first fastener material layer 40 can include a plurality of hook elements 90 on its top surface 44 and the second fastener material layer 50 can include a plurality of loop elements 80 on its bottom surface 52. Certain embodiments including the hook and loop fastener materials can have a low profile with a density of 1700 hooks or greater per square inch of material. The fastener material of the fastener material layers 40, 50 can be incorporated into a nonwoven material or other suitable material. Other embodiments can utilize adhesive bonding, backing adhesive, transfer adhesive, pressure sensitive adhesive, polyurethane medical tape, ultrasonic welding, and/or other like attachment methods to attach the fastener material to a nonwoven or other suitable carrier material. In embodiments, the thickness of the hook and loop fastener material layers 40, 50 with adhesive backing and engaged with one another can range from approximately 0.0465 inches to 0.2500 inches, nominal at approximately 0.053 inches.

Figure 2:
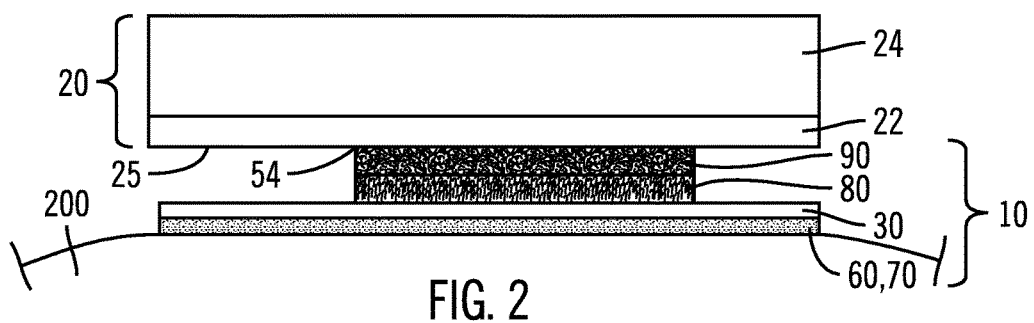
FIG. 2 is a side view of a representation of a multilayer attachment apparatus connected to a medical device in accordance with an embodiment of the present invention.

As shown in embodiments in FIG. 2, the top surface 54 of the second fastener material layer 50 can be connected to a medical device 20 or medical device component 22, 24. In some embodiments, the top surface 54 of the second fastener material layer 50 can include an adhesive material 60 or an adhesive backing to attach to the medical device 20. Adhesive bonding, backing adhesive, transfer adhesive, pressure sensitive adhesive, polyurethane medical tape, ultrasonic welding, and/or other like attachment methods can be used to attach the second fastener material layer 50 to the medical device 20 or medical device component 22, 24. Hence, when the top surface 54 of the second fastener material layer 50 is connected to a medical device 20 or medical device component 22, 24, the medical device 20 or medical device component 22, 24 can be removed from the multilayer attachment apparatus 10 while the nonwoven layer 30 remains attached to the body 200. In the specific embodiment illustrated in FIG. 2, the first medical device component 22 can remain attached to the body 200 via the nonwoven layer 30 while the second medical device component 24 can be removed from the first medical device component 22

As generally shown in the embodiment of FIG. 2, the medical device 20 can include a first component 22 and a second component 24 that are attachable and detachable with one another. In such embodiments, the first component 22 can remain attached to the multilayer attachment apparatus 10 while the second component 24 can be removed from the apparatus 10. As non-limiting examples, the first component 22 can comprise a base and the second component 24 can comprise a housing. For example, an insulin patch pump having a base and a housing can be used with embodiments of the apparatus. As another example, the first component 22 can comprise a first medical device 20 and the second component 24 can comprise a second medical device 20 in a medical device system. Embodiments of the apparatus can work with medical devices including, but not limited to devices or components of a sensor or monitoring system or an infusion medium delivery system. In one embodiment, a second component 24 such as a needle inserting device can be connected to a first component 22 such as a base structure of an infusion delivery device for insertion of a needle, after which the needle inserting device can be removed from the base and replaced with a different second device component 24 such as, but not limited to a reservoir and pump and/or drive device that can be coupled to the base for operation.

Figure 3:
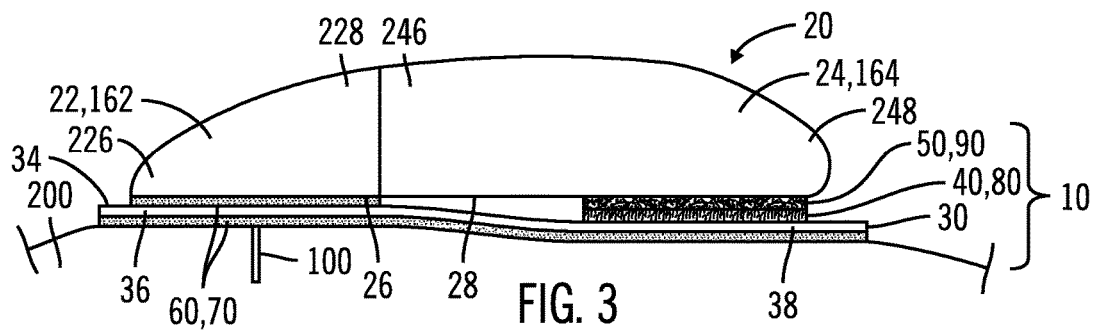
FIG. 3 is a side view of a further representation of a multilayer attachment apparatus connected to a medical device in accordance with an embodiment of the present invention.
Figure 4:
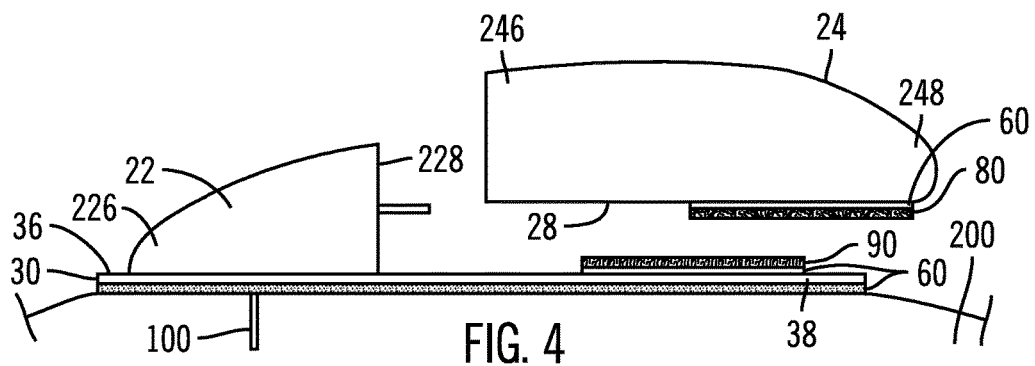
FIG. 4 is a side view of a still further representation of a multilayer attachment apparatus connected to a medical device in accordance with an embodiment of the present invention.

In certain embodiments generally illustrated in FIGS. 3 and 4, the medical device 20 used with the attachment apparatus 10 can include two components 22, 24 arranged horizontally that are attachable and detachable to one another. One component 22 can attach to the body 200 and remain attached to the body 200 while removing the second component 24 from the first component 22 and the apparatus 10. FIG. 3 illustrates an embodiment with the components 22, 24 connected. FIG. 4 illustrates an embodiment with one component 24 removed. In the embodiments shown in FIGS. 3 and 4, the first medical device component 22 can remain attached to the body via the nonwoven layer 30 while the second medical device component 24 can be removed from the apparatus 10 via the second fastener material layer 50 that is removable from the first fastener material layer 40 attached to the nonwoven layer 30 of the apparatus 10.

As shown in the illustrated embodiment in FIG. 3, a first end 36 of the nonwoven layer 30 can connect directly to a first component 22 via adhesive material 60 or an adhesive layer 70 while a second end 38 of the nonwoven layer 30 can connect to a second component 24 via first and second fastener material layers 40, 50 and adhesive material or adhesive layers. In all embodiments herein describing a first end and second end, the first and second connotation is for identification purposes and can be reversed. The second fastener material layer 50 connected to one of the two components 24, and removably connected with the first fastener material layer 40, allows for easy removal of a second component 24 of a medical device 20 from a first component 22 of the medical device 20, while first component 22 can remain attached to the body 200 during the monitoring or treatment operation of the medical device 20. Such embodiments allow for easy removal and/or replacement of one component 24 of a medical device 20 without disruption of the attachment of the other component 22 of the medical device 20 to the body 200, especially when the component attached to the body 200 includes a needle or cannula 100 for fluid delivery or for monitoring a physiological characteristic.

In the exemplary embodiment shown in FIG. 3, the first component 22 of the medical device 20 can be a sensor base 162 having a cannula 100 with a sensor 101 to monitor a physiological characteristic of a user. The second component 24 can be a sensor transmitter 164 to store or provide sensor readings to another device or another component in the sensor system. As a non-limiting example, the user could use the multilayer attachment apparatus 10 and method with a continuous glucose sensor system including but not limited to Medtronic MiniMed, Inc. products such as Sof-Sensor®, Enlite®, iPro®, and MiniLink® transmitter.

As shown in the embodiment in FIG. 3, each first component 22 and second component 24 of the medical device 20 can have a first end 226, 246 and a second end 228, 248. The second end 228 of the first component 22 can be removably connected with the first end 246 of the second component 24. To connect the first component 22 to the nonwoven layer 30 in some embodiments, either at least a portion of the bottom surface 26 of first component 22 can have an adhesive layer 70 or adhesive backing 60 to attach to the top surface 34 of the nonwoven layer 30, or at least a portion of the top surface 34 of the nonwoven layer 30 can have an adhesive layer 70 or adhesive material 60 to attach to the bottom surface 26 of the first component 22. In other embodiments, the adhesive material 60 can be formed in a separate layer that is attached, bonded, or welded to either the at least a portion of the top surface 34 of the nonwoven layer 30 or at least a portion of the bottom surface 25 of the medical device 20.

In the embodiments shown in FIG. 3, the second component 24 can be attached to the nonwoven layer 30 via the first and second fastener material layers 40, 50. The bottom surface 28 of the second component 24 can be connected to the top surface 34 of the nonwoven layer 30 via a second fastener material layer 50 connected to the bottom surface 28 of the second component 24 and a first fastener material layer 40 connected to the top surface 34 of the nonwoven layer 30. Further, the first fastener material layer 40 can include a plurality of loop elements 80 and the second fastener material layer 50 can include a plurality of hook elements 90 in embodiments, as shown in FIG. 3. In other embodiments, the first fastener material layer 40 can include a plurality of hook elements 90 and the second fastener material layer 50 can include a plurality of loop elements 80, as shown in FIG. 4. The plurality of hook and/or loop elements 90, 80 of the first and second fastener material layers 40, 50 can be incorporated into nonwoven material or another suitable material. The first fastener material layer 40 and the second fastener material layer 50 can be removably connected to one another.

Figure 5:
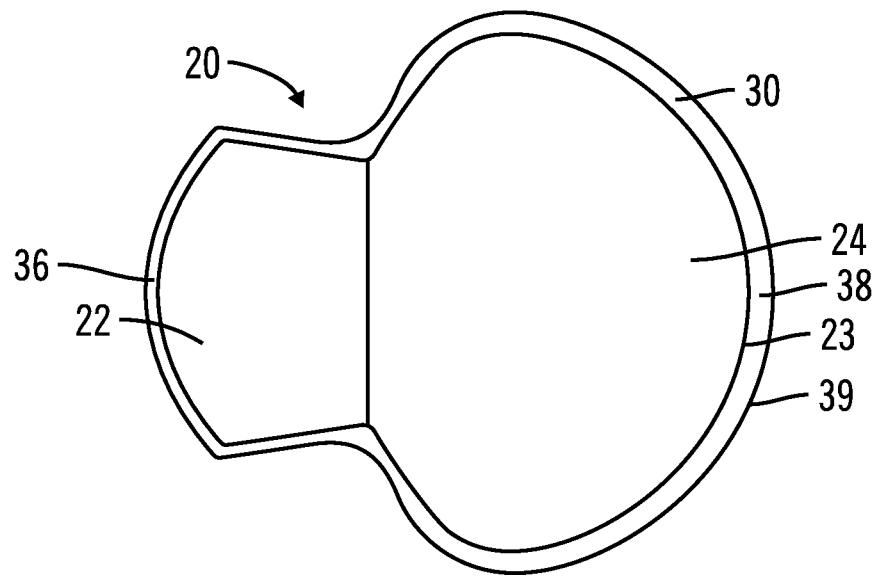
FIG. 5 is a top view of a yet further representation of a multilayer attachment apparatus connected to a medical device in accordance with an embodiment of the present invention.

FIG. 5 illustrates a top view of an embodiment of the multilayer attachment apparatus 10 connected to a medical device 20 having a first medical device component 22 and a second medical device component 24. In some embodiments, the perimeter 39 of the nonwoven layer 30 can be slightly larger and outline about the perimeter 23 or mimic the shape of the perimeter 23 of the medical device 20. In other embodiments, the perimeter 39 of the nonwoven layer 30 can be smaller than or equal to that of the medical device 20, and need not form the same shape as that of the medical device 20.

Figure 13:
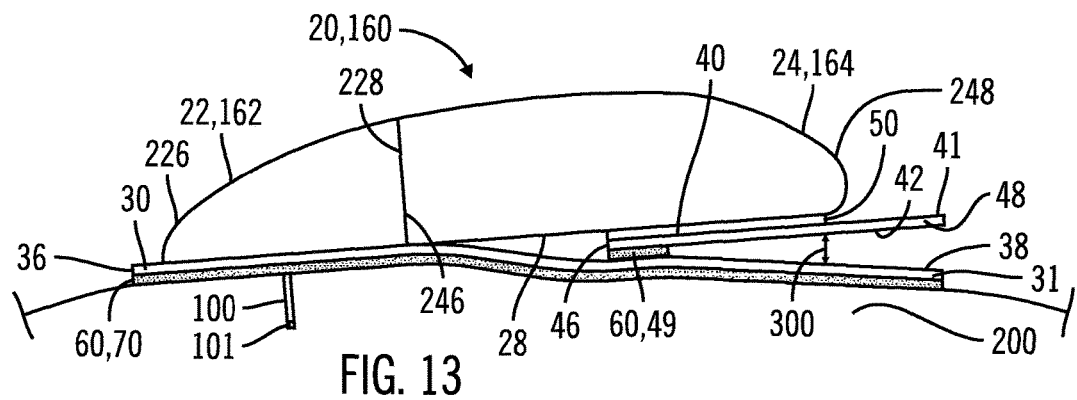
FIG. 13 is a side view of a yet further representation of a multilayer attachment apparatus connected to a medical device in accordance with an embodiment of the present invention.

In an embodiment shown in FIG. 5, a first end 36 of the top surface 34 of the nonwoven layer 30 can be directly attached to a first medical device component 22 via an adhesive material 60 or adhesive layer 70 either on the nonwoven layer or the medical device. The second end 38 of the nonwoven layer 30 can be connected to a second medical device component 24 via the first and second fastener material layers 40, 50 connected to the top surface 34 of the nonwoven layer 30 at the second end 38 of the nonwoven layer 30. Examples of this embodiment are also shown in FIGS. 3, 10 and 13, with the medical device components 22, 24.

Figure 6:
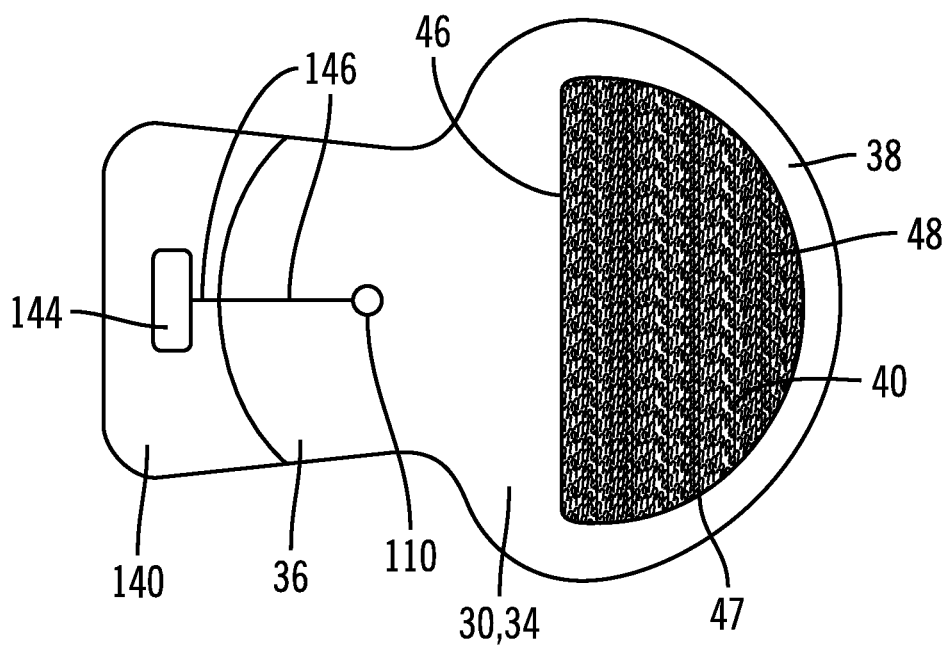
FIG. 6 is a top view of a representation of a removable liner, nonwoven layer, and first fastener material layer of a multilayer attachment apparatus in accordance with an embodiment of the present invention.

FIG. 6 shows a top view of an embodiment of a removable liner 140, nonwoven layer 30, and first fastener material layer 40. As shown in the embodiment illustrated in FIG. 6, the removable liner 140 can include features to assist with assembling the multilayer attachment apparatus 10. In particular embodiments where the apparatus 10 is assembled using a mounting frame, the removable liner 140 can include an aperture 144, a slit 146 and/or other like features to receive a part of the frame during assembly. The nonwoven layer 30 can also include the slit 146 and/or other like features to receive a part of a mounting device during assembly of the multilayer attachment apparatus 10. In addition, the removable liner 140, adhesive material 60 or adhesive layer 70, and nonwoven layer 30 can each include an aperture 110 adapted to receive a cannula 100 or needle when the apparatus 10 is connected to a medical device 20 having a cannula 100 or needle.

In some embodiments, as illustrated by way of example in FIG. 6, the first fastener material layer 40 connected to the nonwoven layer 30 can be connected to or proximate to a second end 38 of the nonwoven layer 30. The surface area of the first fastener material layer 40 can be less than each of the surface area of the nonwoven layer 30 and/or the surface area of the medical device 20 or medical device component 22, 24 to which it is attached. The perimeter 47 of the first fastener material layer 40 can outline within the inside of at least a portion of the perimeter 39 of the nonwoven layer 30 and or the perimeter 23 of the medical device 20 or medical device component 22, 24 to which it may attach. In embodiments, the first and/or a second end 46, 48 of the first fastener material layer 40 can mimic the shape or perimeter 57 of second fastener material layer 50 to which it may attach. In further embodiments, the first fastener material layer 40 can have a semi-circular shape. For example, in the embodiment shown in FIG. 6, the first fastener material layer 40 has a first end 46 having a straight edge and a second end 48 having a curved edge.

Figure 7A:
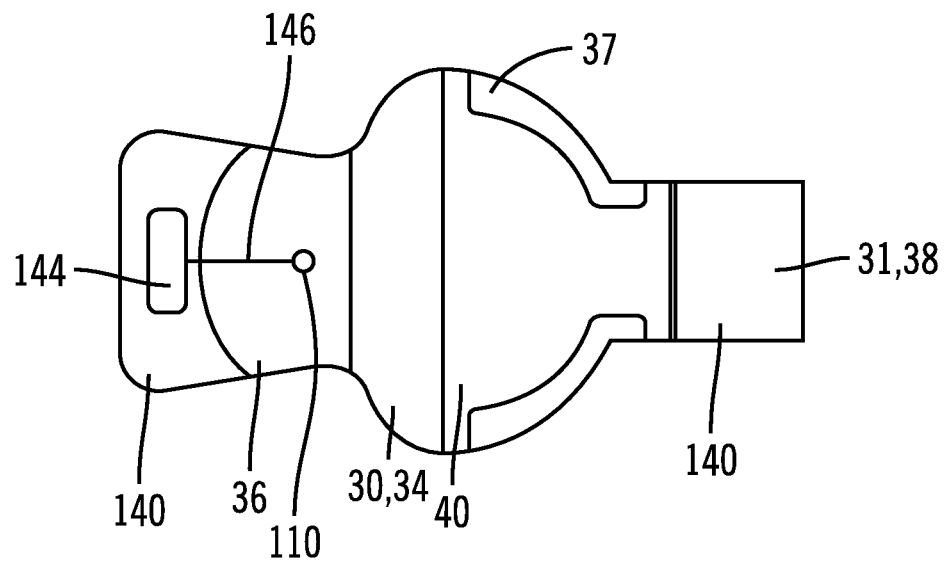
FIG. 7A is a top view of a further representation of a removable liner, nonwoven layer, and first fastener material layer of a multilayer attachment apparatus in accordance with an embodiment of the present invention.
Figure 7B:
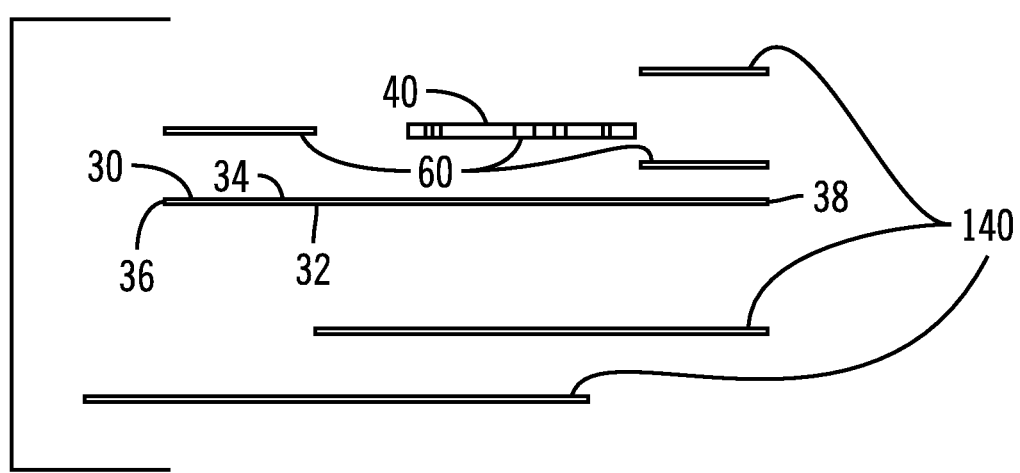
FIG. 7B is an exploded side view of a representation of a removable liner, nonwoven layer, and first fastener material layer of a multilayer attachment apparatus in accordance with the embodiment shown in FIG. 7A.

FIGS. 7A and 7B illustrate a top view and exploded side view, respectively, of at least one removable liner 140, a nonwoven layer 30 and a first fastener material layer 40 according to one embodiment of the invention. In embodiments where the first fastener material layer 40 is not incorporated into the nonwoven layer 30, the nonwoven layer 30 can include a visual guide 37 as shown in FIG. 7A, to indicate where to attach the first fastener material layer 40. In some embodiments, the at least one removable liner 140 can include as many liners necessary to cover each adhesive material 60 portion or layer 70 of the multilayer attachment apparatus 10.

As shown in FIG. 7B, in embodiments the apparatus 10 can include a first, second and third removable liner 140. The first liner can removably cover a first end 36 of the bottom surface 32 of the nonwoven layer 30 having an adhesive backing and the second liner can removably cover a second end 38 of the bottom surface 32 of the nonwoven layer 30 having an adhesive backing 60. A third liner 140 can be included where the nonwoven layer 30 has a tab 31 with adhesive material 60 or an adhesive layer 70 at the second end 38 of top surface 34 of the nonwoven layer 30 in the embodiment, as shown in embodiments in FIGS. 7A and 7B. In specific embodiments, one or more of the removable liners 140 can be folded over themselves so as not to interfere or overlap where the liners can be connected to adhesive 60, 70.

As shown in the embodiment in FIG. 7B, the first end 36 of top surface 34 of the nonwoven layer 30 can include a layer of transfer adhesive and/or a layer of polyurethane medical tape to connect the nonwoven layer 30 to a medical device 20 or a component 22, 24 of a medical device 20. Also shown in the embodiment in FIG. 7B, the first fastener material layer 40 can include an adhesive material 60 or backing on its bottom surface 42 to attach to a user's body. The nonwoven layer 30 can further include a tab 31 with an adhesive material 60 or adhesive layer 70 on the top surface 34 at the second end 38 of the nonwoven layer 30, as shown in FIG. 7B. The adhesive top surface 34 at the second end 38 of the nonwoven layer 30 can attach the tab 31 to a medical device 20 or medical device component 22, 24.

Figure 8:
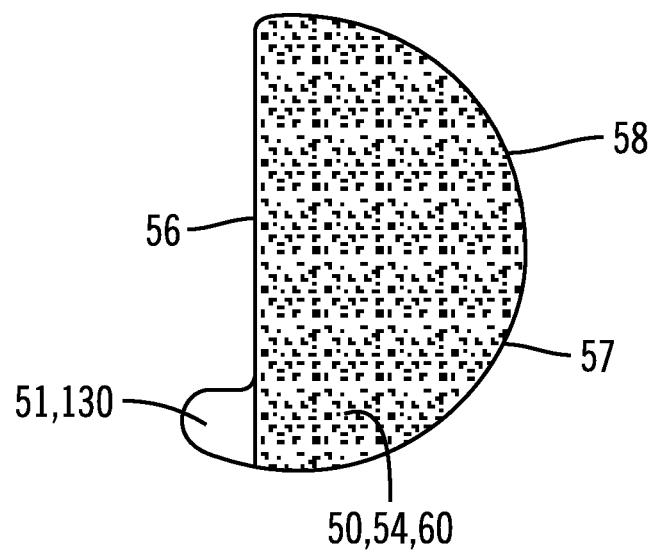
FIG. 8 is a top view of a representation of a second fastener material layer of a multilayer attachment apparatus in accordance with an embodiment of the present invention.
Figure 9:
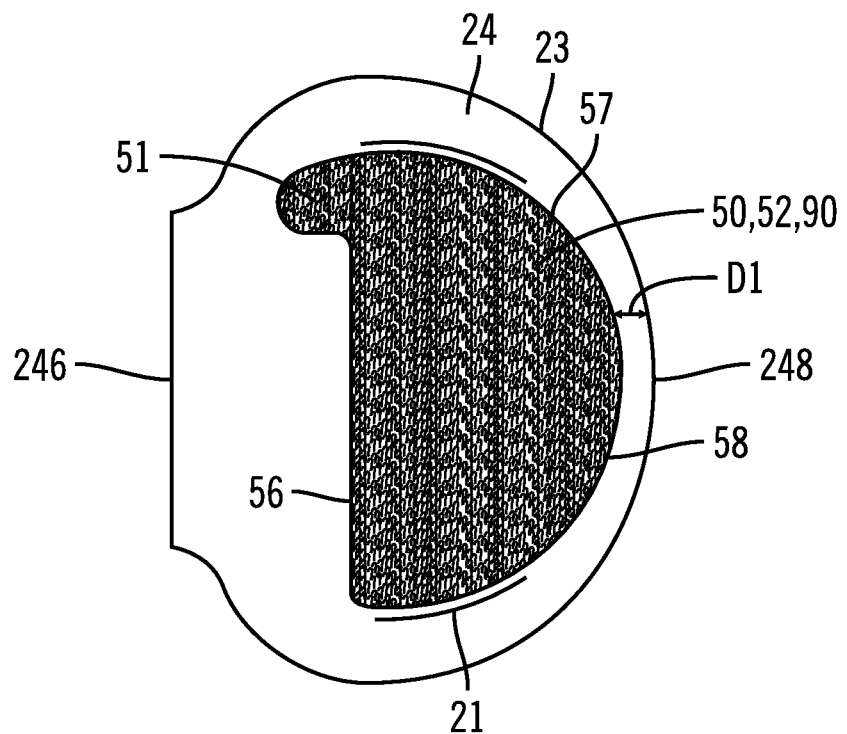
FIG. 9 a bottom view of a representation of a second fastener material layer of a multilayer attachment apparatus connected to a medical device in accordance with an embodiment of the present invention.

As shown in embodiments in FIGS. 8 and 9, the second fastener material layer 50 can have the same or approximately the same surface area and shape or perimeter 57 as the perimeter 47 of the first fastener material layer 40 for removably coupling the two layers together. The second end 58 of the second fastener material layer 50 can also partially resemble the shape or perimeter 23 of the medical device 20 or medical device component 24 and/or the perimeter 39 of the second end 38 of the nonwoven layer 30. In particular embodiments, the second fastener material layer 50 can have a semi-circular shape. For example, the first end 56 can have a straight edge and the second end 58 can have a curved edge. The surface area of the second fastener material layer 50 can be less than each of the surface area of the nonwoven layer 30 and/or the surface area of the medical device 20 or medical device component 22, 24 to which it is connected. In embodiments, the medical device 20 can include a visual guide 21 to indicate where to attach the second fastener material layer 50. The visual guide can be in any form or shape so long as it can indicate where to place the second fastener material layer 50 on the medical device 20 or medical device component 22, 24.

A top view of an embodiment of the second fastener material layer 50 is shown in FIG. 8. In certain embodiments, the top surface 54 of the second fastener material layer 50 can include an adhesive material 60, backing or adhesive layer 70 to attach the second fastener material layer 50 to a medical device 20 or medical device component 22, 24. Embodiments of the second fastener material layer 50 can include a tab 51. In some embodiments, the tab 51 of the second fastener material layer 50 can be located on the first end 56 of the second fastener material layer 50. The top surface 54 of the tab 51 of the second fastener material layer 50 can include a poly film 130 or the like so that the tab 51 will not adhere to the medical device 20 or medical device component 22, 24. The tab 51 can be used to allow the user to easily remove and/or replace the second fastener material layer 50 from the reusable device 20 or device component 22, 24 and the user can then attach a new second fastener material layer 50 to the device or device component.

For example, a user may reuse a medical device 20 or medical device component 22, 24 such as a sensor transmitter 164. With continued use, the fastener material layer 50, and the adhesive between the layer and the device, can become a less effective attachment means as it is exposed to humidity and other detrimental environmental factors. The user can remove the second fastener material layer 50 from the first fastener material layer 40 and then remove the second fastener material layer 50 from the medical device component 24 using the tab 51. Other components of the attachment apparatus 10 can also be replaced as needed so that the attachment apparatus 10 can remain effective.

FIG. 9 illustrates an embodiment of the second fastener material layer 50 attached to a medical device component 24. The top surface 54 of the second fastener material layer 50 is connected to the medical device component 24 and the bottom surface 52 of the second fastener material layer 50 is shown. The bottom surface 52 can include a plurality of hook or loop elements 90, 80 to removably couple with loop or hook elements 80, 90 of top surface 44 of the first material fastener layer 40.

In certain embodiments, the first and second fastener material layers 40, 50 can be positioned on the nonwoven layer 30 and medical device 20 or medical device component 22, 24, respectively, to localize the attachment force where the most load is expected and to accommodate stress factors such as movement of the body 200 while using the attachment apparatus 10. For example, as shown in FIGS. 3, 9, 10, 13 and 15, the second fastener material layer 50 can be positioned on or closer to a second end 248 of a second medical device component 24, or at an end that is distal from where the second medical device component 24 is connected to the first medical device component 22, i.e., an end closer to the perimeter 23 of the medical device 20 or medical device component 24. Likewise, as shown in FIGS. 3, 6, 7, 10, 11 and 13-15, the first fastener material layer 40 can be positioned on or closer to a second end 38 of the nonwoven layer 30 to couple with the second fastener material layer 50 that is positioned similarly on the medical device 20 or medical device component 22, 24.

FIGS. 10-12 illustrate embodiments of the apparatus 10 in which the nonwoven layer 30 includes an extended tab 33. As shown in one embodiment in FIG. 10, the nonwoven layer 30 can connect to a first bottom surface 28 of a medical device component 24 via the first and second fastener material layers 40, 50 at its second end 38 and can simultaneously connect to a second bottom surface 26 of a medical device component 22 at the first end 36 of the nonwoven layer 30. In the particular embodiment shown in FIG. 10, the extended tab 33 on the second end 38 of the nonwoven layer 30 can wrap around the medical device 20 to attach to a top surface 27 of the medical device 20. The extended tab 33 could also attach to a side surface 29 of a medical device 20 or medical device component 24. In embodiments, a top surface 34 of the extended tab 33 can include a fastening material to attach the extended tab 33 to the medical device 20 or medical device component 24.

In certain embodiments, as shown in FIG. 11, the top surface 34 of the extended tab 33 of the nonwoven layer 30 includes an adhesive material 60 to connect to the medical device 20 surface. This embodiment can include a removable liner 140 to cover the adhesive material 60 on the extended tab 33 prior to use. In other embodiments, the extended tab 33 can use a first fastening material or female feature to couple with a second fastening material or male feature on the surface of the medical device 20. In embodiments, as shown in FIG. 12, the bottom surface 32 of the extended tab 33 of the nonwoven layer 30 can include a poly liner 130. In yet further embodiments, the tab 41 of the first fastener material layer 40 can be extended and have similar features to those of the extended tab 33 of the nonwoven layer 30, described above. However, in the embodiment in FIG. 11, the tab 41 on the second end 48 of the first fastener material layer 40 is not extended to the length of the extended tab 33 of the nonwoven layer 30. In embodiments where the nonwoven layer 30 includes an extended tab 33, the extended tab 33 can be attached and detached from a medical device 20 or medical device component 22, 24 to prevent or provide access to the tab 41 of the first fastener material layer 40.

Figure 14:
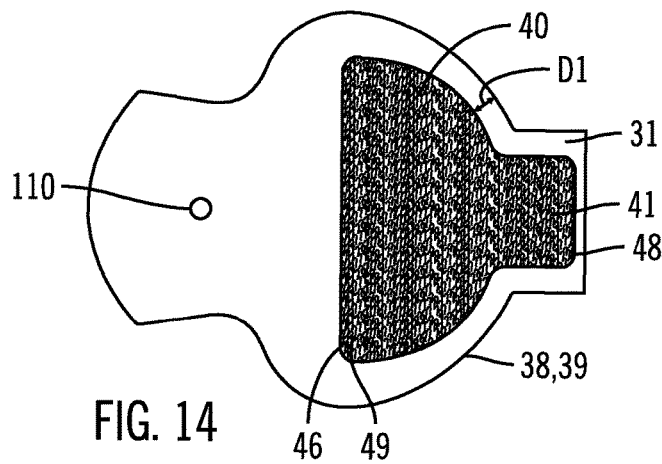
FIG. 14 is a top view of a representation of a nonwoven layer and first fastener material layer of a multilayer attachment apparatus in accordance with an embodiment of the present invention.
Figure 15:
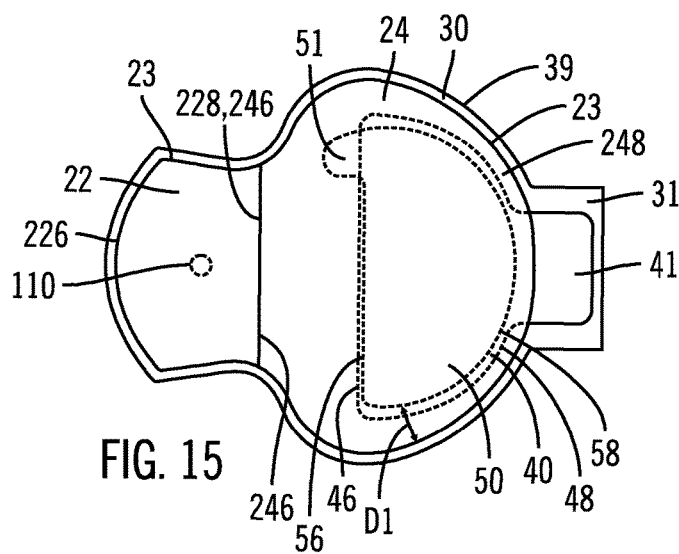
FIG. 15 is a partially transparent top view of a medical device connected to an additional representation of a multilayer attachment apparatus in accordance with an embodiment of the present invention.

FIGS. 13-15 illustrate a specific embodiment of the multilayer attachment apparatus 10 in which only a portion of the first fastener material layer 40 is attached to the nonwoven layer 30. As shown in the embodiments in FIGS. 13 and 14, the first fastener material layer 40 has a first end 46 and a second end 48 and the first fastener material layer 40 is connected only at its first end 46 to the to surface nonwoven layer 30. Thus, the first fastener material layer 40 can include an adhesive material 60 on its bottom surface 42 only at the first end 46 of the first fastener material layer 40. In specific embodiments, the bottom surface 42 of the first fastener material layer 40 can include a strip 49 of adhesive material 60 along its first end 46 having a straight edge. In such embodiments, only the bottom surface 42 of the strip 49 at the first end 46, rather than the entire bottom surface 42 of the first fastener material layer 40, can include an adhesive material or layer 60, 70 to attach to the nonwoven layer 30.

As shown in the embodiment in FIG. 13, the medical device 20 attached to the apparatus 10 includes a first component 22, for example a sensor base 162 including a cannula 100 and sensor 101, and a second component 24, for example a sensor transmitter 164. As a non-limiting example, the medical device can be a glucose monitoring device 160. Each component 22, 24 can have a first end 226, 246 and a second end 228, 248 as shown in the embodiments in FIGS. 13 and 15. The second end 228 of the first component 22 can be removably connected with the first end 246 of the second component 24.

In the embodiments shown in FIGS. 13-15, the second component 24 can be attached to the nonwoven layer 30 via the first and second fastener material layers 40, 50. The bottom surface 28 of the second component 24 can be connected to the top surface 34 of the nonwoven layer 30 via a second fastener material layer 50 connected to the bottom surface 28 of the second component 24 and a first fastener material layer 40 connected to the top surface 34 of the nonwoven layer 30. Further, the top surface 44 of the first fastener material layer 40 can include a plurality of loop elements 80 and the bottom surface 52 of the second fastener material layer 50 can include a plurality of hook elements 90. In other embodiments, the top surface 44 of the first fastener material layer 40 can include a plurality of hook elements 90 and the bottom surface 52 of the second fastener material layer 50 can include a plurality of loop elements 80. The first fastener material layer 40 and the second fastener material layer 50 can be removably connected to one another.

In certain embodiments where the first component 22 includes a sensor 101 to provide a signal indicative of a characteristic of a user. The cannula 100 and/or sensor 101 can be implanted in and/or through subcutaneous, dermal, sub-dermal, inter-peritoneal or peritoneal tissue. Embodiments of a surface mounted sensor could utilize interstitial fluid harvested from underneath the skin. In specific embodiments of the present invention, the sensor 101 is a glucose sensor 101 and can determine glucose levels in the blood and/or body fluids of the user. The sensor can be an electrode-type sensor, or other type of sensor, such as chemical based, optical based or the like. Embodiments may provide sensor readings on an intermittent or continuous basis. The sensor transmitter can store and provide sensor readings to other devices or other components of a sensor system. For example, the transmitter can process and wirelessly transmit sensor signals to a remotely located data receiving device such as a monitor.

In embodiments having a sensor 101, it is important for the first component 22 having a cannula 100 to remain stable against the body 200 to avoid disruption of the sensor 101 during wear and operation of the sensor monitoring. Likewise, if the first component 22 is an infusion delivery device, it would be important for the cannula 100 to remain in position in the body 200 for consistent fluid delivery. In such embodiments, the first component 22 having the cannula 100 can be directly attached to the body 200 via the nonwoven layer 30. To connect the first component 22 to the nonwoven layer 30 in some embodiments, either at least a portion of the bottom surface 26 of first component 22 can have an adhesive layer 70 or adhesive backing to attach to the top surface 34 of the nonwoven layer 30, or at least a portion of the top surface 34 of the nonwoven layer 30 can have an adhesive layer 70 or adhesive material 60 to attach to the bottom surface 26 of the first component 22. In other embodiments, the adhesive material 60 can be formed in a separate layer that is attached, bonded, or welded to either the at least a portion of the top surface 34 of the nonwoven layer 30 or at least a portion of the bottom surface 25 of the medical device 20.

Attachment of the first fastener material layer 40 only at the first end 46 can allow for an adjustable space 300 or room for contours or uneven surfaces of the body 200 when the second medical device component 24 is attached to the nonwoven layer 30 via the first and second fastener material layers 40, 50. Thus, when the medical device 20 has a flat rigid surface that does not align with the contours of the body 200, at least the first component 22 of the medical device 20 can remain closely attached to the body 200 at the first end 36 of the nonwoven layer 30, while the second component 24 of the medical device 20 can adjust and need not remain flat against the body 200 at the second end 38 of the nonwoven layer 30.

Because current adhesive methods used for attachment of medical devices to the body 200 utilize a single attachment method and do not allow for flexibility between a second medical device component 24 and the body 200, the first medical device component 22 having the cannula 100 can be lifted and disrupted easily because the second component 24 is positioned tight against the body 200 and can move with the body 200. For example, when the first and second medical device components 22, 24 are attached with one another, the first medical device component 22 can lift up and away from the body when the second end 248 of the second medical device component 24 is pressed down toward the body.

Embodiments of the new attachment apparatus 10 described herein, utilizing both an adhesive attachment to or proximate to the first end 36 of the nonwoven layer 30 and a hook and loop attachment partially attached to or proximate to a second end 38 of the nonwoven layer 30, allow for a flexible detachable space 300 for movement between a second medical component 24 and the body 200, but not between a first component 22 and the body 200. Because only a first end 46 of a first fastener material layer 40 is attached to the nonwoven layer 30, the apparatus 10 can allow the second device component 24 a space for body contours that are oriented in a direction away from the second device component 24, so that the second device component 24 in line with the first device component 22 and not required to press down to lay flush against the body contour and, as a result, lift the first device component 22 away from the body. However, where there are relatively little contours on the body, the apparatus 10 and device component 24 can also lay flat against the body 200 with no space as if the entire first material layer 40 is attached to the nonwoven layer 30 as in other embodiments. As a result, the multilayer attachment apparatus 10 provides better monitoring or infusion delivery operation of the first component 22 without disruption due to the flexibility and adjustable design that is more forgiving of movement during wear and operation of the attached device.

In clinical studies, the resulting multilayer attachment mechanism provided an unexpected thirty percent improvement of accuracy of sensor readings due to improved attachment of the sensor base 162 and transmitter 164 to the patient body 200 with the attachment apparatus 10 such as the embodiments shown in FIGS. 13-15, compared to prior adhesive attachment methods. Thus, utilizing the apparatus 10 with a sensor and sensor transmitter as described herein results in a method for improved sensor performance and improved sensor accuracy, thereby overcoming problems associated with anchoring rigid inflexible devices to the curved contours of the body. The multilayer attachment apparatus 10 can also provide better wearability. Testing of embodiments of the multilayer attachment apparatus 10 used with a sensor base 162 and sensor transmitter also showed that that apparatus 10 withstood at least seven day soaks in saline solution at 50° Celsius to mimic hot and humid environmental exposure without adhesive delamination.

Because the attachment apparatus 10 and medical device 20 can be worn for several days at a time next to the body and can be discreetly worn under clothing, at least one of the fastener material layers may occasionally require replacement due to body humidity and sweat or environmental factors decreasing the effectiveness of the fastener. At least one fastener material layer can therefore require replacement more often than the durable medical device 20 or medical device component 22, 24 to which it is attached. In specific embodiments, at least one of the fastener material layers can be replaceable. In the embodiments shown in FIGS. 9 and 15, the second fastener material layer 50 includes a tab 51 to facilitate application and removal and replacement, if necessary, of the second fastener material layer 50 from the second component 24. Testing of the multilayer attachment apparatus 10 has shown that the second fastener material layer 50 having an adhesive backing can be removed from the medical device 20 without residue after seven days of attachment. The present invention can therefore allow for continued and repeated use of one sensor transmitter 164 while the sensor base 162, cannula 100, and/or the multilayer attachment apparatus 10 can be replaced occasionally if needed.

In additional embodiments, the first fastener material layer 40 can include a tab 41. As shown in FIG. 14, the first fastener material layer 40 can include a tab 41 at the second end 48 of the first fastener material layer 40. The tab 41 of the first fastener material layer 40 can be held by the user while removing the second fastener material layer 50 and the medical device 20 or medical device component 22, 24, if attached to the second fastener material layer 50. In embodiments where the first fastener material layer 40 includes a tab 41, the nonwoven material layer 30 can include a tab 31 of approximately the same length.

Also shown in FIG. 15, specific embodiments of the invention include a nonwoven layer 30 that can have a surface area and a perimeter 39 that is larger than and outlines outside the surface area and perimeter 23 of the medical device 20. The transparent view through the medical device components 22, 24, show the first and second fastener material layers 40, 50 attaching the second medical device component 24 to the nonwoven layer 30. The surface area and perimeter of each of the first and second fastener material layers 40, 50 can be smaller than those of the medical device 20 or medical device component 24 attached. In the embodiments shown in FIGS. 13-15, the overall surface area of each of the fastener material layers is approximately one half of the surface area of the medical device 20 and approximately two-thirds the surface area of the second component 24. In particular embodiments, the coupling surface area of the first and second fastener material layers 40, 50 can be 0.25-0.5 inch$^2$, nominal at 0.4 inch$^2$ and the minimum load can be two and one half pounds of force, nominal of six pounds force. Overall, the shapes of the fastener material layers 40, 50 provide sufficient attachment but still detach when required.

In certain embodiments, the shape of at least one of the fastener material layers 40, 50 can at least partially outline inside the perimeter 23 of the medical device 20 or medical device component 24 attached. In the embodiments shown in FIGS. 13-15, the fastener material layers 40, 50 can have generally semi-circular shapes. As shown, the first ends 46, 56 of each of the first and second fastener material layers 40, 50 can have straight edges and the second ends 48, 58 of each of the first and second fastener material layers 40, 50 can have rounded edges that match the shape of the perimeter 23 of the second end 248 of the second component 24.

In specific embodiments, the first fastener material layer 40 can be positioned on the nonwoven layer 30 at a distance D1 of 0.75 cm or greater from inside the perimeter 39 at the second end 38 of the nonwoven layer 30 and the second fastener layer can be positioned on the second component 24 at a distance D1 of 0.75 cm or greater from inside the perimeter 23 of the second end 248 of the second component 24. The second fastener material layer 50 can have an adhesive material 60 on its top surface 54 to connect to the bottom surface 28 of the second component 24.

Methods for using the multilayer attachment apparatus 10 with a medical device 20 or medical device component 22, 24 are also described herein by way of the embodiments described above. An example method for anchoring a medical device 20 having a first component 22 and a second component 24 to a body 200 of a user can generally comprise providing a nonwoven layer 30 having a first end 36, a second end 38, a top surface 34 and a bottom surface 32. In embodiments, at least a portion of the bottom surface 32 of the nonwoven layer 30 can include an adhesive material 60 adapted to attach to the body 200. At least a portion of the top surface 34 at the first end 36 of the nonwoven layer 30 can include an adhesive material 60 adapted to attach to the first component 22 of the medical device 24. At least a portion of the top surface 34 at the second end 38 of the nonwoven layer 30 can be connected to a first fastener material layer 40 having a top surface 44 that can include a plurality of loop elements 80.

To mate with the first fastener material layer 40, a second fastener material layer 50 having a top surface 54 and a bottom surface 52 can be provided. In some embodiments, the bottom surface 52 of the second fastener material layer 50 can include a plurality of hook elements 90 and at least a portion of the top surface 54 of the second fastener material layer 50 can includes an adhesive material 60 to attach to the second component 24 of the medical device 20.

The next step of the method can comprise either attaching the first component 22 of the medical device 20 to at least a portion of the top surface 34 at the second end 38 of the nonwoven layer 30 and attaching the bottom surface 32 of the nonwoven layer 30 to the body 200 of the user, or attaching at least a portion of the top surface 54 of the second fastener material layer 50 to the second component 24 of the medical device 20. These steps can be reversed and do not need to be performed in a particular order. Lastly, the bottom surface 52 of the second fastener material layer 50 can be connected to the top surface 44 of the first fastener material layer 40. In other embodiments, the first and second fastener material layers 40, 50 can be connected prior to attaching the nonwoven layer 30 to the body 200.

Embodiments of methods for attaching the fastener material layers and adhesives can include providing a guide 21, or outline pattern, on the medical device 20 or medical device component 22, 24 to which the user may attach the second fastener material layer 50 having an adhesive backing 60. The pattern on the device may be filled in with color or comprise and dashed or solid outlined shape. A non-limiting example of a guide 21 on a medical device 20 is shown in FIG. 9. In other embodiments, the second fastener material layer 50 having an adhesive material 60 on its top surface 54 can include a sheet of second fastener material layer 50 having an adhesive that can include a perforated pattern in which the user may apply the second fastener material layer 50 to the medical device 20 or component 22, 24, and subsequently remove the material outside of the perforation pattern while the required portion of the material remains attached to the device. In alternative embodiments, the second fastener material layer 50 may be the same shape and less than or equal to the size of the device, and the user can line up the second fastener material layer 50 with the outer perimeter 23 of the device or a set distance D1 within the inside of the perimeter 23 of the device to attach the layer to the device, as illustrated in FIG. 9.

The methods can have fewer or additional steps to encompass all embodiments of the multilayer attachment apparatus 10 used with or without a medical device 20 and/or medical device components 22, 24 as described herein. The method steps described need not be performed in any particular order.

While the description above refers to particular embodiments of the present invention, it will be understood that many modifications can be made without departing from the spirit thereof. The accompanying claims are intended to cover such modifications as would fall with the true scope and spirit of the present invention. The presently disclosed embodiments are therefore to be considered in all respects as illustrative and not restrictive, the scope of the invention being indicated by the appended claims, rather than the foregoing description, and all changes within the meaning and range of equivalency of the claims are therefore intended to be embodied therein.

What is claimed is:

1. A multilayer attachment apparatus for anchoring a medical device to a body of a user, the medical device including a cannula capable of being inserted into the body of the user, the multilayer attachment apparatus comprising:

a first layer, a second layer, and a third layer, wherein all three layers are separate from the medical device;

the first layer having a first end, a second end, a bottom surface and a top surface, wherein at least a portion of the top surface of the first layer proximate to the first end of the first layer is connectable to at least a portion of a bottom surface of a first component of the medical device including the cannula capable of being inserted into the body of the user;

the second layer having a first end, a second end, a bottom surface and a top surface;

the third layer having a bottom surface and a top surface, wherein at least a portion of the bottom surface of the second layer is connected to at least a portion of the top surface of the first layer proximate to the second end of the first layer, at least a portion of the top surface of the second layer and the bottom surface of the third layer are removably connected to one another, and at least a portion of the top surface of the third layer is connectable to at least a portion of a bottom surface of a second component of the medical device, such that the first end of the first layer is directly connectable to the first component including the cannula capable of being inserted into the body of the user while the second end of the first layer is connectable to the second component via the second and third layers between the first layer and the second component, and further wherein only the first end of the bottom surface of the second layer is connected to at least a portion of the top surface of the first layer such that an adjustable space is formed between the first layer and the second layer to enable movement of the second component relative to the second end of the first layer;

further wherein, when the medical device is anchored to the body of the user:
the cannula is inserted in the body of the user and the first component is attached to the body of the user via the first layer, and the second component is moveably attached to the first layer and body via the first, second and third layers;

further wherein, when the medical device is anchored to the body of the user and the second component is detached from the first component:
the first layer remains attached to the first component and the second layer; and
the third layer remains attached to the second component and detaches from the second layer;
such that the cannula remains inserted in the body of the user and the first component remains attached to the body via the first layer, when the second component is detached from the body.

2. The multilayer attachment apparatus of claim 1, wherein at least a portion of the bottom surface of the first layer includes an adhesive material.

3. The multilayer attachment apparatus of claim 2, further including at least one removable liner to cover at least a portion of the bottom surface of the first layer to protect the adhesive prior to use.

4. The multilayer attachment apparatus of claim 3, wherein the at least one removable liner includes a tab.

5. The multilayer attachment apparatus of claim 1, further including:
an adhesive layer having a bottom surface and a top surface, wherein at least a portion of the bottom surface of the first layer is connected to the top surface of the adhesive layer.

6. The multilayer attachment apparatus of claim 5, including the medical device, wherein each of the first layer and the adhesive layer include an aperture to receive the cannula.

7. The multilayer attachment apparatus of claim 5, further including at least one removable liner to cover at least a portion of the bottom surface of the adhesive layer to protect the adhesive prior to use.

8. The multilayer attachment apparatus of claim 1, wherein the second layer includes a plurality of loop elements and the third layer includes a plurality of hook elements.

9. The multilayer attachment apparatus of claim 1, wherein the second layer includes a plurality of hook elements and the third layer includes a plurality of loop elements.

10. The multilayer attachment apparatus of claim 1, including the medical device, wherein the first layer includes an aperture to receive the cannula.

11. The multilayer attachment apparatus of claim 1, wherein the first layer further includes a poly layer on at least a portion of the top surface of the first layer.

12. The multilayer attachment apparatus of claim 1, wherein the first layer includes a tab.

13. The multilayer attachment apparatus of claim 1, wherein the first layer includes an extended tab, wherein a top surface of the extended tab includes a fastening material connectable to a surface of the medical device.

14. The multilayer attachment apparatus of claim 13, wherein a bottom surface of the extended tab includes a poly layer.

15. The multilayer attachment apparatus of claim 1, wherein the second layer includes a tab.

16. The multilayer attachment apparatus of claim 1, wherein at least a portion of the bottom surface of the second layer includes an adhesive material.

17. The multilayer attachment apparatus of claim 1, wherein the third layer includes a tab.

18. The multilayer attachment apparatus of claim 1, wherein at least a portion of the top surface of the third layer includes an adhesive material.

19. The multilayer attachment apparatus of claim 1, including the medical device, wherein the medical device is a glucose monitoring device;
wherein the first component is a sensor base; and
wherein the second component is a sensor transmitter.

20. The multilayer attachment apparatus of claim 1, wherein the perimeter of the third layer substantially covers the bottom surface of the second component when connected to the second component.

21. The multilayer attachment apparatus of claim 1, wherein the first layer includes a nonwoven material.

22. The multilayer attachment apparatus of claim 1, wherein, when at least a portion of the top surface of the first layer proximate to the first end of the first layer and at least a portion of the top surface of the third layer are connected to at least a portion of the bottom surfaces of the first and second components of the medical device, respectively, the first layer remains connected to the bottom surface of the first component and the third layer remains connected to the bottom surface of the second component when the third layer is removed from the second layer.

23. The multilayer attachment apparatus of claim 1, wherein at least a portion of the top surface of the first layer proximate to the first end of the first layer includes an adhesive material.

24. The multilayer attachment apparatus of claim 1, wherein the first, second, and third layers are thin, flexible layers.

25. A system for improved glucose sensor monitoring device performance and accuracy comprising:
a glucose monitoring device including a sensor transmitter and a sensor base, the sensor base having a cannula and glucose sensor;
an attachment apparatus to attach the glucose monitoring device to a body of a user, the attachment apparatus including:

a first layer, a second layer, and a third layer, wherein all three layers are separate from the glucose monitoring device;

the first layer having a first end, a second end, a bottom surface and a top surface, the bottom surface of the first layer including an adhesive to attach the first layer to the body, and at least a portion of the top surface of the first end of the first layer is connected to a bottom surface of the sensor base including the cannula and glucose sensor capable of being inserted into the body of the user and the first end of the first layer includes an aperture to receive the cannula;

the second layer having a first end, a second end, a bottom surface and a top surface; and the third layer having a bottom surface and a top surface, wherein at least a portion of the bottom surface of the second layer is connected to at least a portion of the top surface of the second end of the first layer, at least a portion of the top surface of the second layer and the bottom surface of the third layer are removably connected to one another, and at least a portion of the top surface of the third layer is connected to a bottom surface of the sensor transmitter such that the first end of the first layer is directly connected to the sensor base including the cannula and glucose sensor capable of being inserted into the body of the user while the second end of the first layer is connected to the sensor transmitter via the second and third layers between the first layer and the sensor transmitter, and further wherein only the first end of the bottom surface of the second layer is connected to at least a portion of the top surface of the first layer such that an adjustable space is formed between the first layer and the second layer to enable movement of the sensor transmitter relative to the second end of the first layer further wherein, when the glucose monitoring device is anchored to the body of the user:
  the cannula is inserted in the body of the user and the sensor base is attached to the body of the user via the first layer, and the sensor transmitter is moveably attached to the first layer and body via the first, second and third layers;

further wherein, when the glucose monitoring device is anchored to the body of the user and the sensor transmitter is detached from the sensor base:
the first layer remains attached to the sensor base and the second layer; and
the third layer remains attached to the sensor transmitter and detaches from the second layer;
  such that the cannula remains inserted in the body of the user and the sensor base remains attached to the body via the first layer, when the sensor transmitter is detached from the body.

26. A method for anchoring a medical device having a first component and a second component to a body of a user, the first component including a cannula capable of being inserted into the body of the user, comprising the steps of:

providing a first layer, a second layer and a third layer, wherein all three layers are separate from the medical device;

the first layer having a first end, a second end, a top surface and a bottom surface, wherein at least a portion of the bottom surface includes an adhesive material, wherein at least a portion of the top surface of the first layer proximate to the first end of the first layer includes an adhesive material to attach to a bottom surface of the first component of the medical device including the cannula capable of being inserted into the body of the user;

the second layer having a first end, a second end, a bottom surface and a top surface, wherein at least a portion of the top surface of the first layer proximate to the second end of the first layer is connected to only the first end of the bottom surface of the second layer;

the third layer having a top surface and a bottom surface, wherein the bottom surface of the third layer is removably connectable with the top surface of the second layer and wherein at least a portion of the top surface of the third layer includes an adhesive material;

attaching the bottom surface of the first component of the medical device to at least a portion of the top surface of the first layer proximate to the first end of the first layer;

attaching at least a portion of the top surface of the third layer to a bottom surface of the second component of the medical device;

attaching the bottom surface of the first layer to the body of the user; and attaching the bottom surface of the third layer to the top surface of the second layer such that the first end of the first layer is directly connected to the first component including the cannula capable of being inserted into the body of the user while the second end of the first layer is connected to the second component via the second and third layers between the first layer and the second component, and further wherein connection of only the first end of the bottom surface of the second layer to at least a portion of the top surface of the first layer forms an adjustable space between the first layer and the second layer to enable movement of the second component relative to the second end of the first layer;

further wherein, when the medical device is anchored to the body of the user:
  the cannula is inserted in the body of the user and the first component is attached to the body of the user via the first layer, and the second component is moveably attached to the first layer and body via the first, second and third layers;

further wherein, when the medical device is anchored to the body of the user and the second component is detached from the first component:
  the first layer remains attached to the first component and the second layer; and
  the third layer remains attached to the second component and detaches from the second layer;
  such that the cannula remains inserted in the body of the user and the first component remains attached to the body via the first layer, when the second component is detached from the body.

* * * * *